(12) United States Patent
Jeppson

(10) Patent No.: US 9,114,204 B2
(45) Date of Patent: Aug. 25, 2015

(54) APPARATUS AND METHOD FOR NASAL RINSING

(71) Applicant: Nathan Blake Jeppson, Herriman, UT (US)

(72) Inventor: Nathan Blake Jeppson, Herriman, UT (US)

( * ) Notice: Subject to any disclaimer, the term of this patent is extended or adjusted under 35 U.S.C. 154(b) by 136 days.

(21) Appl. No.: 13/828,735

(22) Filed: Mar. 14, 2013

(65) Prior Publication Data

US 2014/0276624 A1 Sep. 18, 2014

(51) Int. Cl.
*A61M 3/02* (2006.01)

(52) U.S. Cl.
CPC ........... *A61M 3/0262* (2013.01); *A61M 3/0279* (2013.01); *A61M 2210/0618* (2013.01)

(58) Field of Classification Search
USPC ............ 128/200.14, 203.22; 604/36, 39, 151, 604/275, 514
See application file for complete search history.

(56) References Cited

U.S. PATENT DOCUMENTS

| | | | |
|---|---|---|---|
| 3,522,806 A * | 8/1970 | Szekely | 128/200.18 |
| 6,520,384 B2 | 2/2003 | Mehta | |
| 6,558,344 B2 * | 5/2003 | McKinnon et al. | 604/35 |
| 6,669,059 B2 | 12/2003 | Mehta | |
| 6,688,497 B2 | 2/2004 | Mehta | |
| 2010/0095957 A1 * | 4/2010 | Corbacho | 128/200.14 |
| 2010/0114016 A1 * | 5/2010 | Gallo et al. | 604/73 |
| 2010/0199984 A1 * | 8/2010 | Williams et al. | 128/200.23 |
| 2011/0319840 A1 * | 12/2011 | Hair | 604/275 |
| 2012/0090620 A1 * | 4/2012 | Deutsch | 128/207.15 |
| 2013/0319412 A1 * | 12/2013 | Glynn | 128/203.21 |
| 2014/0121592 A1 * | 5/2014 | Rubin et al. | 604/30 |
| 2014/0243794 A1 * | 8/2014 | Halskov et al. | 604/514 |
| 2014/0303565 A1 * | 10/2014 | Kubo et al. | 604/208 |

* cited by examiner

*Primary Examiner* — Gerald Landry, II
(74) *Attorney, Agent, or Firm* — Morriss O'Bryant Compani, PC

(57) ABSTRACT

An apparatus and method for dispensing a saline solution for nasal rinsing includes using a container having a bottom for resting on a surface and a top defining an opening. A pump having a pump housing is disposed within the container and is coupled to the opening of the container. A pump handle is coupled to a pump shaft, which is in turn coupled to the pump housing. The pump handle is coupled to a plunger disposed within the pump housing. An elongate flexible tube is coupled at a first end to the pump handle. A nozzle configured for mating with a nostril of a user is coupled to a second end of the flexible tubing. Pumping the handle causes the saline solution to flow through the nozzle under controlled pressure into a nasal passage of a user.

20 Claims, 8 Drawing Sheets

APPARATUS AND METHOD FOR NASAL RINSING

BACKGROUND

1. Field of the Invention

This invention relates generally to devices and methods for rinsing nasal passages and more specifically to devices and methods for providing a pressurized flow of a saline solution into and through a nasal passage.

2. State of the Prior Art

The paranasal sinuses are a group of four paired air-filled spaces that surround the nasal cavity and are located above and between the eyes and behind the ethmoid sinuses. The maxillary, frontal, ethmoid and sphenoid sinuses are named for the facial bones in which they are located. The maxillary sinuses, also called the maxillary antrechea and the largest of the paranasal sinuses, are located under the eyes in the maxillary bones of the face. The frontal sinuses are located superior to the eyes in the frontal bone, which forms the hard part of the forehead. The ethmoid sinuses are formed from several discrete air cells within the ethmoid bone between the nose and eyes. The sphenoid sinuses are located in the sphenoid bone at the center of the skull base under the pituitary gland.

The paranasal air sinuses are lined with respiratory epithelium and are joined to the nasal cavity by small orifices called ostia. The nasal passage runs from the nostrils to the pharynx. The ostia become blocked easily by allergic inflammation, or by swelling in the nasal lining that occurs with a cold. When this occurs, normal draining of mucus within the sinuses is disrupted, and sinusitis may occur. Rhinitis is another condition resulting from inflammation of the mucosa of a nasal passage.

Both sinusitis and rhinitis can result from exposure to viruses, bacteria, fungi or allergens, as well as exposure to smoke cold viruses, allergies to various allergens, smoke or other air pollutants or contaminants. When rhinitis occurs, common symptoms include stuffy nose, runny nose and post-nasal drip. The most common kind of rhinitis is allergenic rhinitis, which is usually triggered by airborne allergens such as pollen and dander. Allergic rhinitis may cause additional symptoms, such as sneezing and nasal itching, coughing, headache, fatigue, malaise and cognitive impairment. The allergens may also affect the eyes, causing watery, reddened or itchy eyes and puffiness around the eyes. When sinusitis occurs, whether acute or chronic, symptoms may include headache/facial pain or pressure of a dull, constant, or aching sort over the affected sinuses. This pain is typically localized to the involved sinus and may worsen when the affected person bends over or when lying down. Pain often starts on one side of the head and progresses to both sides. Acute and chronic sinusitis may be accompanied by thick nasal discharge that is usually green in color and may contain pus and/or blood. Often a localized headache or toothache is present. Infection of the eye socket is possible, which may result in the loss of sight and is accompanied by fever and severe illness.

These conditions are often treated with drugs such as decongestants that cause vasoconstriction in the sinuses. The goal most treatment is to prevent or reduce the symptoms caused by the inflammation of affected tissues. Intranasal corticosteroids are also used for conditions caused by allergens. Other measures that are often used include antihistamines, cromolyn and leukotriene receptor antagonists. Non-pharmacologic therapies, such as Nasal irrigation is another technique used to rinse the sinuses in order to remove mucus, allergens and contaminants from the sinus and nasal cavities.

Nasal rinsing or lavage often uses a saline solution dispensed into the nasal passage to cleanse and wash away mucus and allergy creating particles and irritants. Such nasal rinsing allows the sinuses to drain normally and often reduces the inflammation of the mucus membrane. One such apparatus and method for nasal rinsing is disclosed in U.S. Pat. No. 6,520,384 issued on Feb. 18, 2003, to Mehta, the entirety of which is incorporated by this reference. FIG. 1 is an illustration of the device set forth in the '384 patent, which includes a container 1 having flexible sidewalls 2 and a removable cap 3. The cap 3 has a rounded convex upper portion 4 curving away from an opening at the cap's uppermost surface and has a conduit 5 in the cap's interior. The conduit 5 extends into the container 1 when the device is fully assembled. The sidewalls 2 of the container, filled with a saline solution, are compressed to urge the saline solution through the conduit 5 and through the opening 6 in the cap and into a nasal passage, the cap 3 being pressed against a nostril.

The devices illustrated in FIG. 1 has several limitations, however, including a limitation of the amount of saline solution that can be forced from the container with each squeeze of the container. Moreover, because the device requires a squeezing of the sidewalls to expel the saline solution, it is difficult to control the pressure and thus the flow rate of solution being expelled from the device in order to provide a steady flow of solution into a nasal cavity. Moreover, the device necessarily provides saline solution in quick bursts and therefore does not provide continuous flow of solution over any extended period of time to provide continuous flushing or rinsing of the nasal passage. Furthermore, the size of the container to be hand held necessarily limits the amount of saline solution that can be provided in each container and therefore often requires multiple preparations to be made for each rinsing operation. Because of these limitations, it is often the case that during use a significant amount of saline solution is wasted. Moreover, the configuration of the device can result in contaminated material being drawn into the container during use.

Thus, there is a need in the art to provide a more effective device for nasal rinsing that allows a user to control the rate of flow of solution from the device over a period of time, that can provide a large volume of solution into a nasal cavity in a short period of time, that allows the user to control the flow rate of the solution into the nasal passage and that prevents contaminated solution from reentering the container.

SUMMARY OF THE INVENTION

Accordingly, the present invention provides an improved apparatus for nasal rinsing. The apparatus is configured for dispensing a solution for nasal rinsing and comprises a container having a bottom for resting on a surface and a top defining an opening. The container contains a saline solution for rinsing a nasal passage. A pump having a pump housing is disposed within the container and is coupled to the opening of the container. A pump handle is coupled to a pump shaft that is coupled to the pump housing. The pump handle is coupled to a plunger disposed within the pump housing. An elongate flexible tube is coupled at a first end to the pump handle and a nozzle configured for mating with a nostril of a user is coupled to a second end of the flexible tubing. Pumping the handle causes the saline solution to flow through the nozzle under controlled pressure into a nasal passage of a user.

In one embodiment, a first one-way valve is disposed within the housing proximate a distal end thereof for preventing flow of solution from the pump housing into the container when the pump handle is depressed. The first one-way valve comprises a first ball valve comprising a ball, a ball seat and a ball retaining structure with the ball residing between the ball seat and the ball retaining structure and movable between an open position and a closed position.

A second one-way valve is in fluid communication with the pump shaft for preventing flow of solution from the elongate flexible tubing into the pump housing when the pump shaft is extended from the pump housing. The second one-way valve comprises a second ball valve comprising a ball, a ball seat and a ball retaining structure with the ball residing between the ball seat and the ball retaining structure and movable between an open position and a closed position.

A biasing member is disposed within the pump housing between a distal end of the pump housing and the plunger for forcing the plunger away from the distal end of the housing so as to cause the plunger to return to a first position after each pump by the user.

In another embodiment, a volume defined within the pump housing between the distal end of the housing and the plunger is at least one of about 20 cc, about 30 cc or about 50 cc.

In another embodiment, the pump is configured to allow a single pump to be between about 0.1 and 2.0 seconds.

In another embodiment, the elongate flexible tube has a length of approximately 24 inches.

In another embodiment, a nozzle grip is coupled to the nozzle with a section of flexible tubing. The nozzle grip is positioned proximate the nozzle.

The present invention also includes a method of dispensing a solution for nasal rinsing, which comprises preparing a saline solution in a container having a bottom for resting on a surface and a top defining an opening. The container contains the saline solution for rinsing a nasal passage. A nozzle configured for mating with a nostril of a user is placed against a nostril. The nozzle is coupled to an elongate flexible tube, which is coupled to the pump. Pumping the pump handle of the pump causes the saline solution to flow through the nozzle under controlled pressure into a nasal passage of a user.

In one embodiment of the method, pumping the pump handle is performed at a rate of between about 0.1 and 2 seconds per pump.

In another embodiment, the pumping causes a flow of approximately 20 to 50 mL of saline solution to flow through the nozzle during each pump.

In another embodiment, the pumping is repeated at a rate of about 0.25 seconds per pump.

In another embodiment, about 20 mL and about 50 mL of solution is expelled per pump.

In yet another embodiment, repeatedly pumping the pump causes approximately 300 mL of solution to be pumped into the nostril of the user after approximately 10 pumps.

In still another embodiment, the method includes placing the nozzle against the other nostril of the user and repeatedly pumping the pump so that approximately 300 mL of solution is pumped into the other nostril of the user.

In yet another embodiment, the user grasps a nozzle grip coupled to the nozzle to hold the nozzle against the nostril of the user.

In still another embodiment, the container is placed on a surface adjacent a sink, the nostril of the user is placed over the sink and the solution is allowed to flow from the nostril against which the nozzle is placed through the nasal passages of the user, out the opposite nostril of the user and into the sink.

In another embodiment, the saline solution is formed from water and dry ingredients in the form of iodized salt and sodium bicarbonate in a water to dry ingredient ratio of approximately 100:1.

These and other aspects of the present invention may be realized in an improved apparatus for nasal rinsing that allows for a controlled and continuous flow of saline solution into a nasal passage of a user as shown and described in the following figures and related description.

BRIEF DESCRIPTION OF THE DRAWINGS

When considered in connection with the following illustrative figures, a more complete understanding of the present invention may be derived by referring to the detailed description. In the figures, like reference numbers refer to like elements or acts throughout the figures. Various embodiments of the present invention are shown and described in reference to the numbered drawings wherein.

Figure 1:
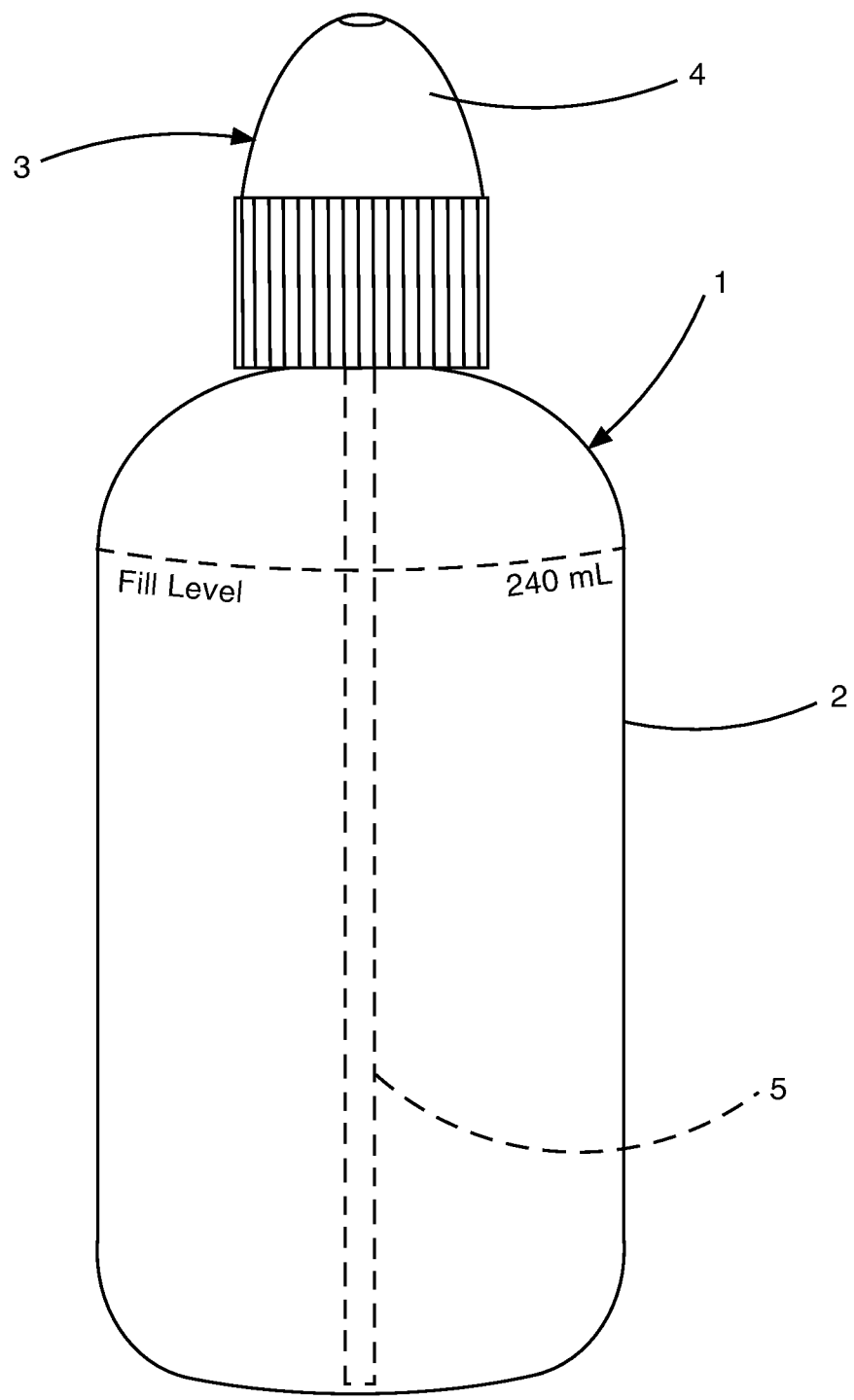
FIG. 1 shows a front side view of a prior art device for nasal rinsing.

It will be appreciated that the drawings are illustrative and not limiting of the scope of the invention, which is defined by the appended claims. The embodiments shown accomplish various aspects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention. Elements and acts in the figures are illustrated for simplicity and have not necessarily been rendered according to any particular sequence or embodiment.

DETAILED DESCRIPTION OF THE ILLUSTRATED EMBODIMENTS

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims. Unless specifically noted, it is intended that the words and phrases in the specification and the claims be given their plain, ordinary, and accustomed meaning to those of ordinary skill in the applicable arts. It is noted that the inventor can be his own lexicographer. The inventor expressly elects, as her own lexicographer, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventor's intent and desire that the simple, plain and ordinary meaning to the terms be applied to the interpretation of the specification and claims.

The inventor is also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventor is fully informed of the standards and application of the special provisions of 35 U.S.C. §112, ¶6. Thus, the use of the words "function," "means" or "step" in the Detailed Description of the Invention or claims is not intended to somehow indicate a desire to invoke the special provisions of 35 U.S.C. §112, ¶6, to define the invention. To the contrary, if the provisions of 35 U.S.C. §112, ¶6 are sought to be invoked to define the inventions, the claims will specifically and expressly state the exact phrases "means for" or "step for" and the specific function (e.g., "means for filtering"), without also reciting in such phrases any structure, material or act in support of the function. Thus, even when the claims recite a "means for . . ." or "step for . . ." if the claims also recite any structure, material or acts in support of that means or step, or that perform the recited function, then it is the clear intention of the inventor not to invoke the provisions of 35 U.S.C. §112, ¶6. Moreover, even if the provisions of 35 U.S.C. §112, ¶6 are invoked to define the claimed inventions, it is intended that the inventions not be limited only to the specific structure, material or acts that are described in the illustrated embodiments, but in addition, include any and all structures, materials or acts that perform the claimed function as described in alternative embodiments or forms of the invention, or that are well known present or later-developed, equivalent structures, material or acts for performing the claimed function.

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. Thus, the full scope of the inventions is not limited to the examples that are described below.

Figure 2:
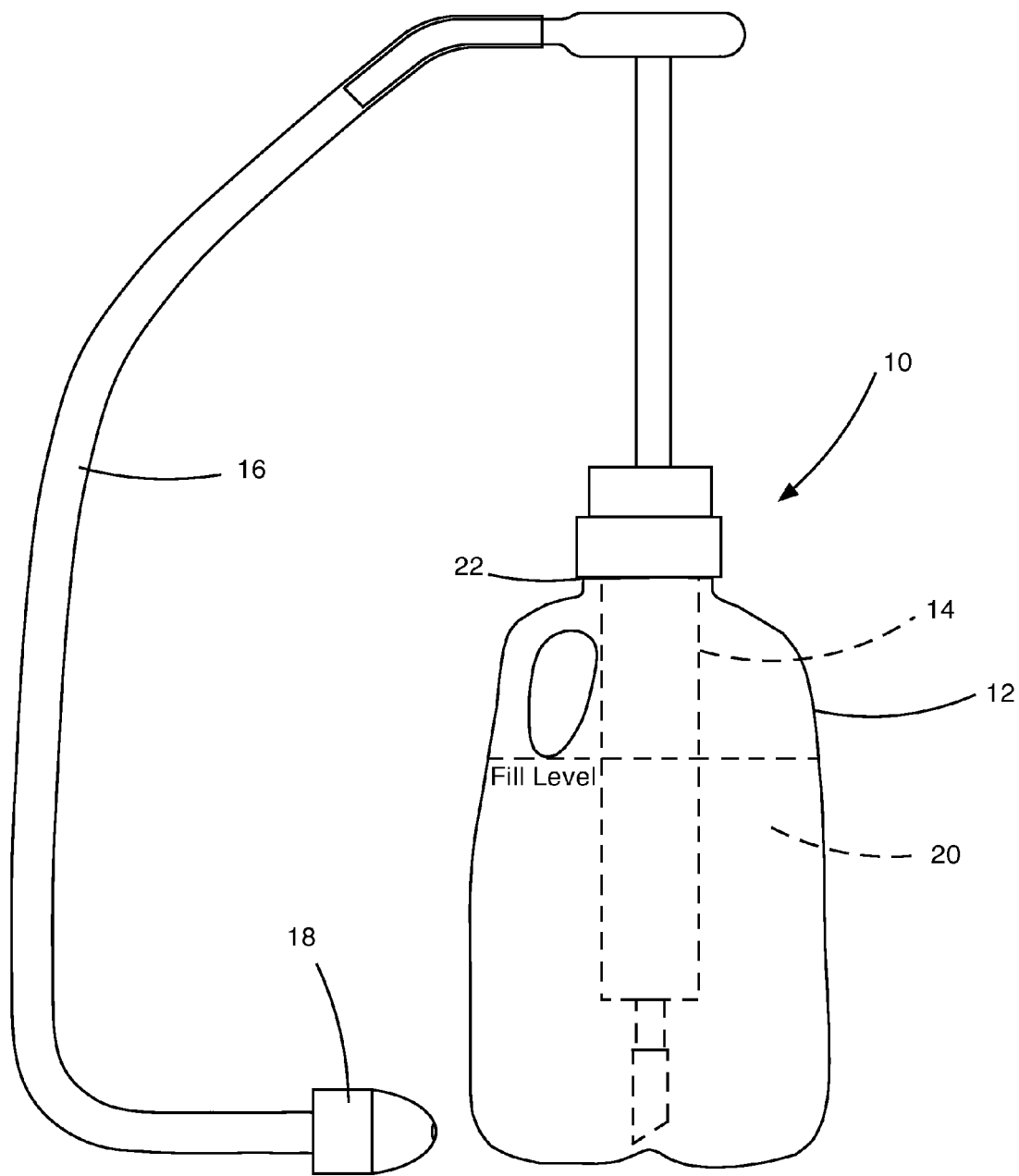
FIG. 2 shows a front side view of an apparatus for nasal rinsing according to the principles of the present invention.

FIG. 2 illustrates an apparatus, generally indicated at 10, for nasal rinsing in accordance with the principles of the present invention. The apparatus 10 comprises a container 12, a hand pump 14 coupled to the container, a length of flexible tubing 16 coupled to the pump 14 and a nozzle 18 coupled to a free end of the tubing 16. The container 12 is of a size that when filled to the Fill Level will allow several pumps from the pump 14 before the container needs to be refilled.

The container can be filled with saline solution 20 that may include various ingredients known in the art, such as the saline solutions described in U.S. Pat. No. 6,520,384, previously discussed. The Fill Level of the container is positioned below the top end 22 of the container a distance sufficient to allow for displacement of the solution 20 when the pump 14 is inserted into the container 12 so that the solution 20 does not overflow the container 12 when the pump is inserted.

The container 12 may be of a sufficiently large volume to allow for enough solution 20 to be prepared and stored in the container 12 for use in several separate nasal rinses. This is especially possible with the apparatus 10 of the present invention as the pump 14 is configured to prevent a flow of solution back into the container 12 once the solution 20 flows into the tubing 16. With the prior art system described in U.S. Pat. No. 6,520,384, air is drawn back through the nozzle after each squeeze of the container, necessarily resulting in the remaining solution in the container to be contaminated and thus requiring an unused solution to be discarded so as to prevent reinfection in subsequent uses of the prior art apparatus. Thus, as will be described in detail herein, the pump 14 is provided with a one-way valve that allows solution 20 to flow into the tubing 16 while preventing solution 20 from reentering the pump.

The tubing 16 is formed from a flexible material such as rubber or plastic, for example flexible clear PVC or vinyl tubing. In one embodiment, the tubing 16 is formed from a clear plastic tubing that allows the user to see the flow of solution and that the solution is not being drawn back into the pump 14 during use that could indicate a malfunction of the one-way valve. The tubing 16 has a length that is sufficient to allow placement of the container 12 on a surface adjacent a wash basin or sink and that allows a user to position the nozzle 18 against a nostril while placing the head of the user over the wash basin or sink. For example, the flexible tubing may have a length of between about 12 inches and 36 inches with a better length of approximately 24 inches. In such a position, when the solution 20 is pumped through the nozzle 18, the resulting expelled solution that exits the free nostril will flow into the wash basin or sink to thereby limit any mess from the expelled solution. In addition, because only the nozzle 18 and the tubing 16 adjacent the nozzle 18 are positioned proximate the nostril of the user, only the nozzle 18 and adjacent tubing 16 will be exposed to any expelled solution 20 that may contain material collected from the nasal passage of the user. As such, after use, the user need only clean the nozzle 18 and adjacent tubing 16 prior to storage and subsequent reuse.

Figure 3:
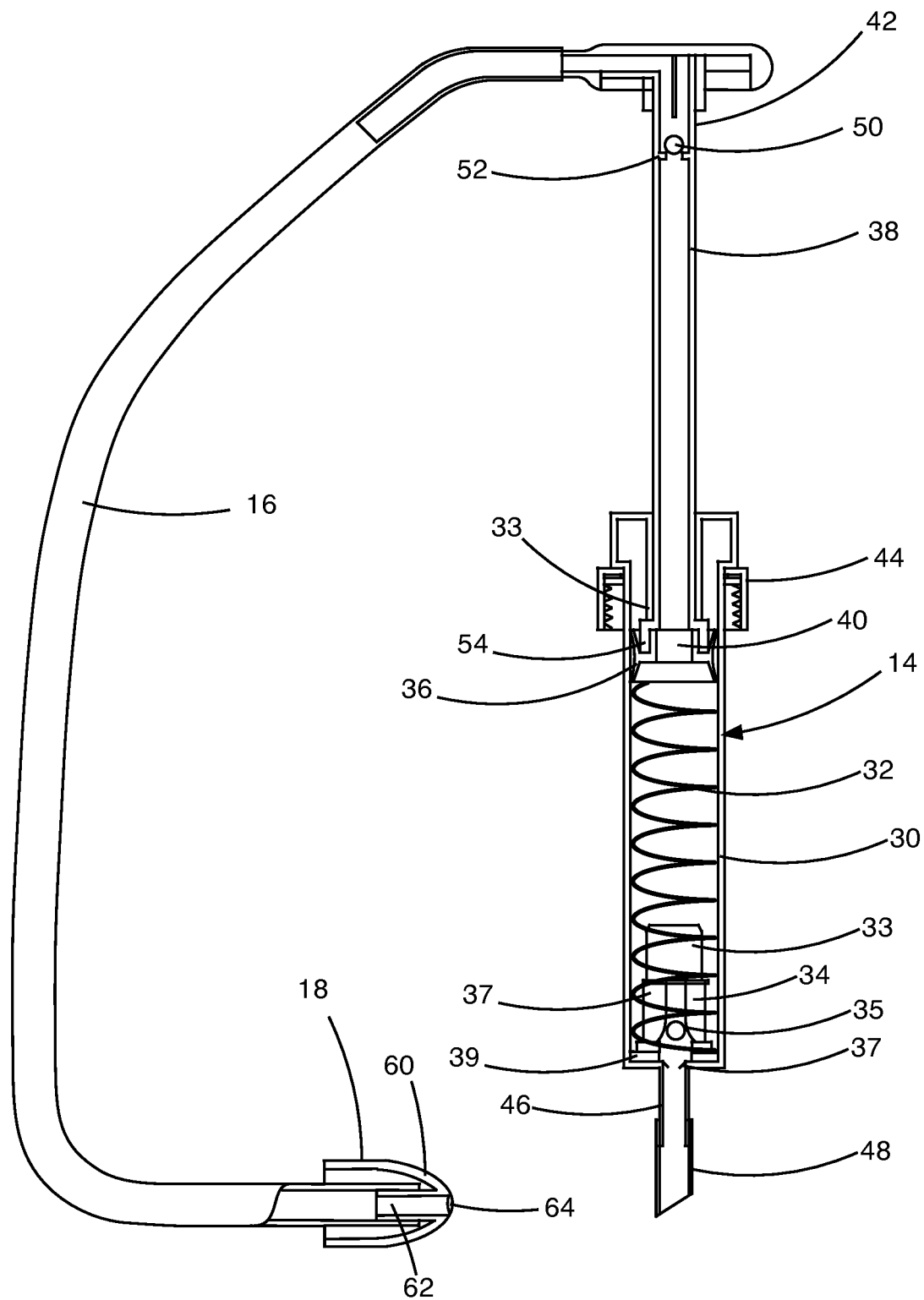
FIG. 3 shows a partial cross-sectional side view of a pump for use with the apparatus for nasal rinsing illustrated in FIG. 1 in accordance with the principles of the present invention.

As shown in FIG. 3, the pump 14 is comprised of a pump housing 30 in the form of a hollow cylindrical body within which is positioned a biasing member 32 in the form of a coil spring, a plunger stop 33 and ball valve 34 adjacent a distal end of the housing 30. A plunger 36 is coupled to a distal end of an elongate hollow pump shaft 38. The plunger 36 has an outer diameter approximately equal to an inner diameter of the housing 30. The plunger 36 has a ring-like configuration with a central aperture 40 in fluid communication with the housing 30 and the pump shaft 38 so that as the pump shaft 38 is depressed, the ball valve 34 will close and solution contained within the pump housing 30 will flow through the aperture 40 of the plunger 36 through the pump shaft 38, through a second ball valve 42, through tubing 16 and out of the nozzle 18. The pump housing 30 has an inside diameter of approximately ¾ to 1 inch, with a particular embodiment having an inside diameter of ⅞ inch and a length of approximately 5 to 5½ inches. The pump shaft 38 has a length of about 4 inches to allow between about 3 to 3½ inches of travel of the plunger 36 within the housing 30 for pumping a sufficient volume (between about 50 cc and 20 cc) of solution with each pump.

An internally threaded retaining ring 44 is rotatably attached proximate an upper or proximal end of the housing 30. The retaining ring 44 is configured to be threadedly attached to the container 12 (see FIG. 2) so as to secure the pump 14 to the container 12 during use and/or storage while allowing the pump 14 to be easily removed from the container 12 in order to refill or wash the container 12 as desired.

As further illustrated in FIG. 3, when the plunger 36 is raised within the housing 30, the ball (which may be formed of a metal or plastic sphere) 35 of the ball valve 34 moves away from the ball seat 37 formed in the distal end of the housing 30 in the exit tube 46 of the pump 14. The ball 35 is retained by a plurality of curved ball retaining members 37 that are integrally formed with the plunger stop 33 and extend downwardly to a support ring 39 that is positioned adjacent the bottom of the housing 30. The support ring 39 is held against the bottom of the housing 30 by the spring 32. The retaining members 37, which may include four such members in the form of longitudinally extending vanes, essentially form a cage around the ball 35 while allowing a flow of solution through the tubing 46 from the housing 30 as the ball is drawn away from the ball seat 37 to be positioned between and temporarily retained by the retaining members 37. The spring 32 is thus in a compressed state even when the plunger 36 is in an uppermost position.

An angled tube 48 is coupled to the distal end of the exit tube 46 having a length sufficient to be positioned proximate the bottom of the container 12 when the retaining ring 44 is attached to the top of the container 12. The tube 48 is angled so as to allow a flow of solution into the tube 48 even if the distal end of the tube 48 is in contact with the bottom of the container 12. Simultaneously, the ball 50 of the ball valve 42 is in contact with the ball seat 52 to prevent any significant flow of solution that may be contained within the tubing 16 from flowing back into the pump 14 that could otherwise contaminate unused solution that may be contained within the pump 14 or the container 12.

The distal end of the pump shaft 38 includes an abutment surface or stop 54 that abuts against an upper retaining portion 56 of the housing 30 that prevents the plunger 36 from exiting the top of the housing 30 when the pump shaft 38 is fully extended.

The nozzle 18 includes an outer arcuate nozzle body 60 sized to be placed against a nozzle of a user without the entire nozzle being placeable within the nostril of the user. In other words, the widest portion of the nozzle body 60 may be between 2.5 and 3 inches so as to be substantially larger than a nostril of the user so that only the tip portion of the nozzle body 60 can be positioned within the nozzle. This size and shape of the nozzle body provides a good seal between the nostril of the user and the nozzle 18. Extending from the proximal end of the nozzle body 60 on an inside thereof, an attachment tube 62 is provided to mate with the tube 16. The attachment tube 62 is hollow and in fluid communication with the nozzle orifice 64 and the tube 16. The nozzle 18 is attached to the tubing with a friction fit so as to be removable for cleaning separate and apart from the tubing 16.

Figure 4:
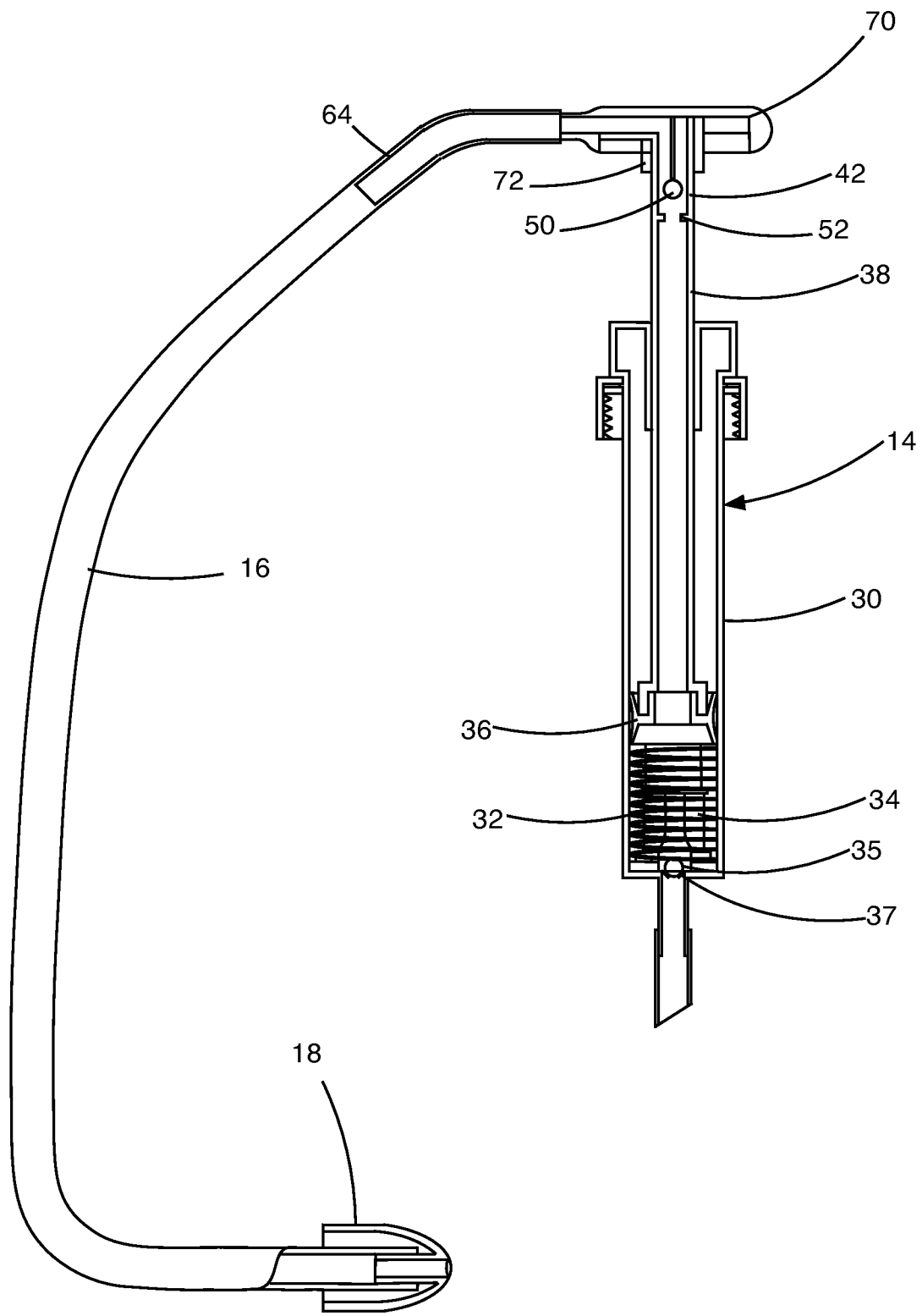
FIG. 4 shows a partial cross-sectional side view of the pump shown in FIG. 3 in a second depressed position in accordance with the principles of the present invention.

As further illustrated in FIG. 4, when the plunger 36 is depressed with the pump shaft 38 and the spring 32 is collapsed, solution contained within the housing 30 is prevented from flowing out the exit tube 46 as the ball 35 engages the ball seat 37 and is thus forced through the plunger 36, through the interconnecting pump shaft 38, through the ball valve 42 out of the exit tube 64, through tubing 16 and finally out of the nozzle 18. The ball 50 of ball valve 42 is retained between a closed position (as shown in FIG. 3) and an open position as illustrated by a post 66 that extends from a pump pressing member or handle 68. The handle 68 is comprised of a generally cylindrical housing 70 having a first tube portion 72 configured for coupling with the pump shaft 38 and a second tube portion 74 integrally formed therewith extending at a right angle to the first tube portion 72 configured for coupling to the tubing 16. As solution flows through the pump shaft 38 and into the ball valve 42, the solution can then flow out of the second tube portion 74 and into the tube 16.

The plunger 36 is generally cylindrical in shape and includes a radial convex flexible side 80 that form a seal between the housing 30 and the plunger 36 so as to prevent solution from flowing between the plunger 36 and the housing 30. When the handle 68 is released, the plunger 36 is automatically forced by the spring 32 to the top end of the housing 30. The pressure differential inside the housing 30 causes the ball 50 to become seated with the ball seat 52 and opens the ball valve 34 thereby drawing solution into the housing 30 while preventing solution in the tubing 16 from entering the pump 14.

Figure 5:
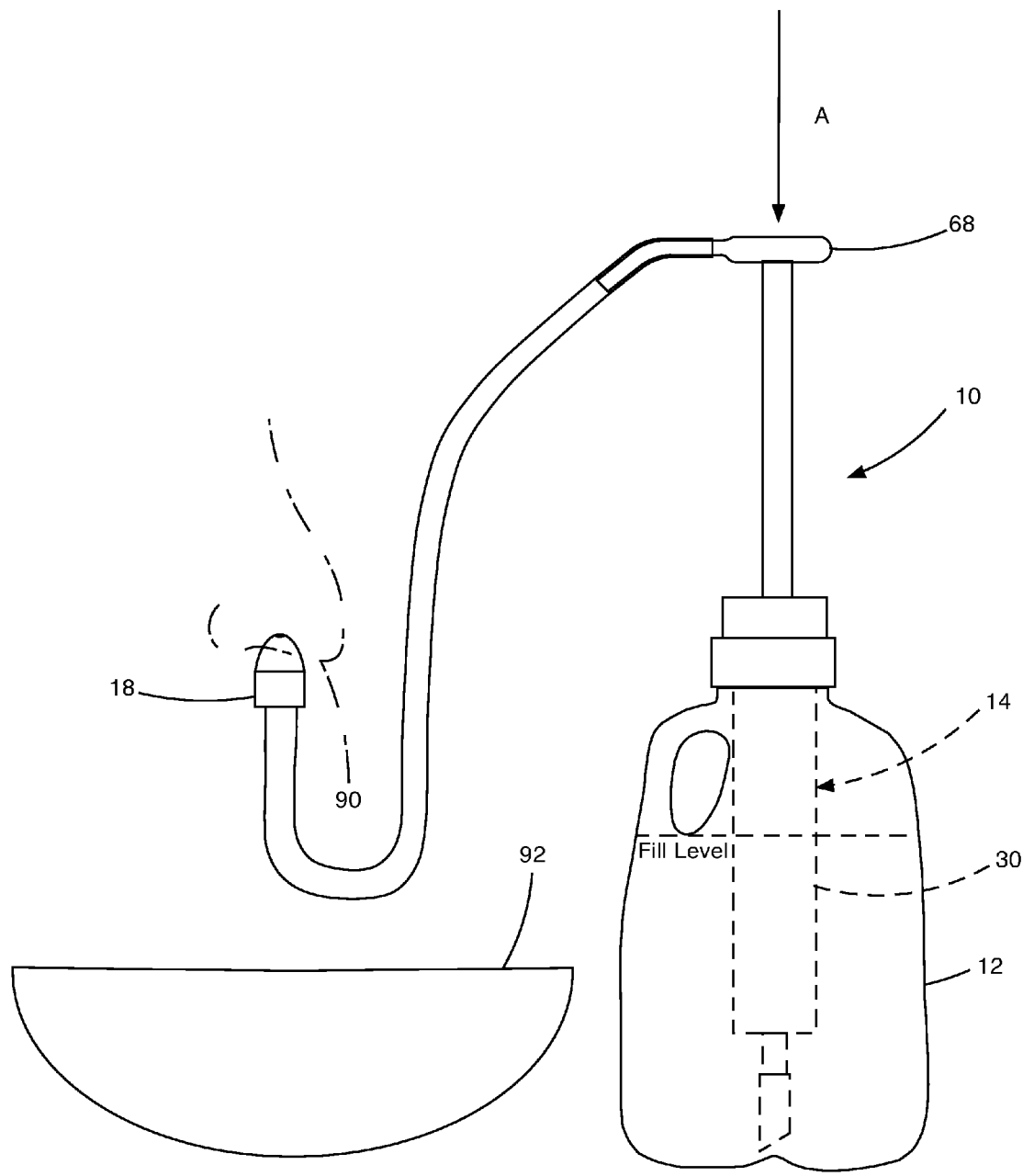
FIG. 5 shows a front side view of the apparatus illustrated in FIG. 1 in use and in a first position in accordance with the principles of the present invention.
Figure 6:
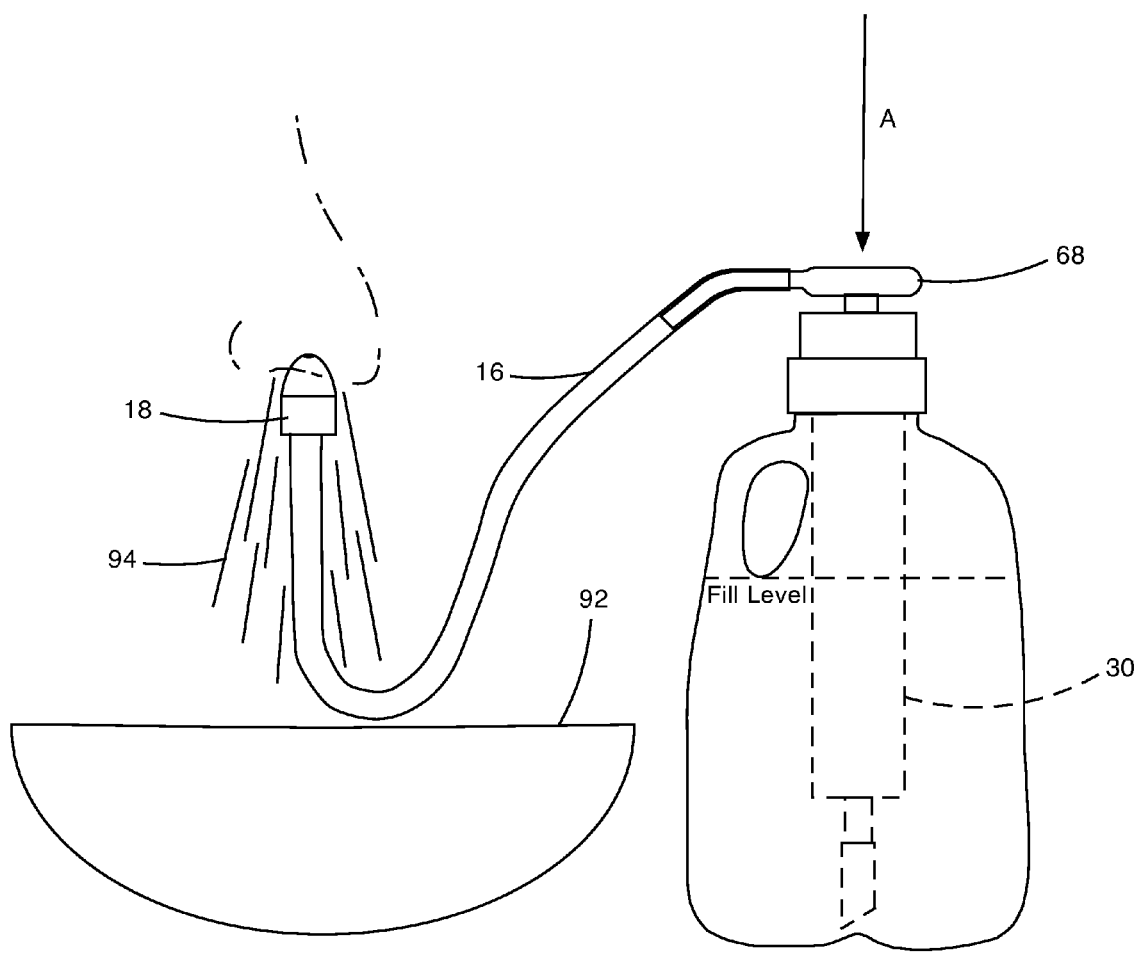
FIG. 6 shows a front side view of the apparatus illustrated in FIG. 5 in use and in a second position in accordance with the principles of the present invention.

FIGS. 5 and 6 better illustrate a method of using a nasal rinse pump 10 according to the principles of the present invention. As shown in FIG. 5, the nozzle 18 is placed against a nostril 90 of a user so as to form a seal between the nozzle and the nostril 90. The tubing 16 is sufficient long enough to have the container 12 and pump 14 positioned adjacent or proximate a wash basin or sink 92. So that the user can position their face over the sink 92. The pump handle 68 is then depressed as shown by arrow A. When the pump 14 is empty, the first depression of the handle 68 will result in only a flow of air.

As the pump handle 68 is allowed to extend after being depressed, the pump 14 then draws solution 20 from the container 12 into the pump housing 30 at which time the level of solution in the container 12 will necessarily lower. As shown in FIG. 6, when the handle 68 is depressed as shown by arrow A, the solution that has been previously drawn into the pump housing 30 is forced into the tubing 16 and out through the nozzle 18. The solution will then flow through the nasal passages of the user and exit through the user's other nostril and/or out of the mouth. Because the user can position their nostrils, mouth and the nozzle 18 over the sink 92, the used solution 94 will then flow directly into the sink 92 with little or no mess.

Each subsequent pump of the handle 68 causes the flow of a relatively specific amount of solution to flow into the nostril of the user, especially after the second pump when both the pump housing 30 and the tube 16 are full of unused solution. In one embodiment, the size of the pump housing and travel of the plunger relative to the pump housing 16 is such that approximately 30 mL (or 30 cc) of solution is expelled from the nozzle 18 with each pump. Repeated and rapid pumps can result in a nearly continuous nasal flush. Likewise, by varying the speed by which the handle 68 is depressed, the flow rate and thus the comfort level of the user can be adjusted to a desired level according to user preference. Thus, the user can vary the rate of each pump to between 2 seconds, for a slow flow of solution, to about 0.1 seconds for an aggressive flow of solution into the nasal passages of the user. Ideally, a user will use approximately 300 mL of solution for rinsing through each nostril for a total of 600 mL of solution being used for each treatment. The pump is capable of dispensing 25 to 30 mL of solution with each pump with each dose of 25 to 30 mL of solution being delivered over a 0.25-0.5 second interval. The container of the present invention is capable of holding several treatments so that a relatively large batch of solution can be made and stored for multiple treatments.

The saline solution used may be a combination of dry ingredients of iodized salt and sodium bicarbonate in a 2:1 ratio. The dry ingredients are mixed with distilled or boiled water in a ratio of ⅛ cup to 1 gallon of water or about a 1% (0.78%) solution. By providing a container of at least one gallon, a gallon of solution, minus the volume of the pump can be prepared and used over a period of time if desired by a user. Otherwise, the size of the container could be configured for approximately 600 mL of solution to be used in a single treatment with each subsequent treatment requiring solution to be prepared. In that case, for example, a gallon of solution can be separately prepared and then poured into a smaller container for use with the pump. The remaining solution in the gallon container can be retained and stored for future use. To accommodate one gallon of solution prepared from a gallon jug of distilled water, the threaded retaining ring 44 shown in FIG. 3 may be configured to screw onto a standard gallon jug, such as a standard jug of distilled water. Otherwise, the container may have any opening and interconnection between the container and the pump so as to retain the pump relative to the container during use and that allows the pump to be selectively removed after use to refill and or clean the container and pump.

Figure 7:
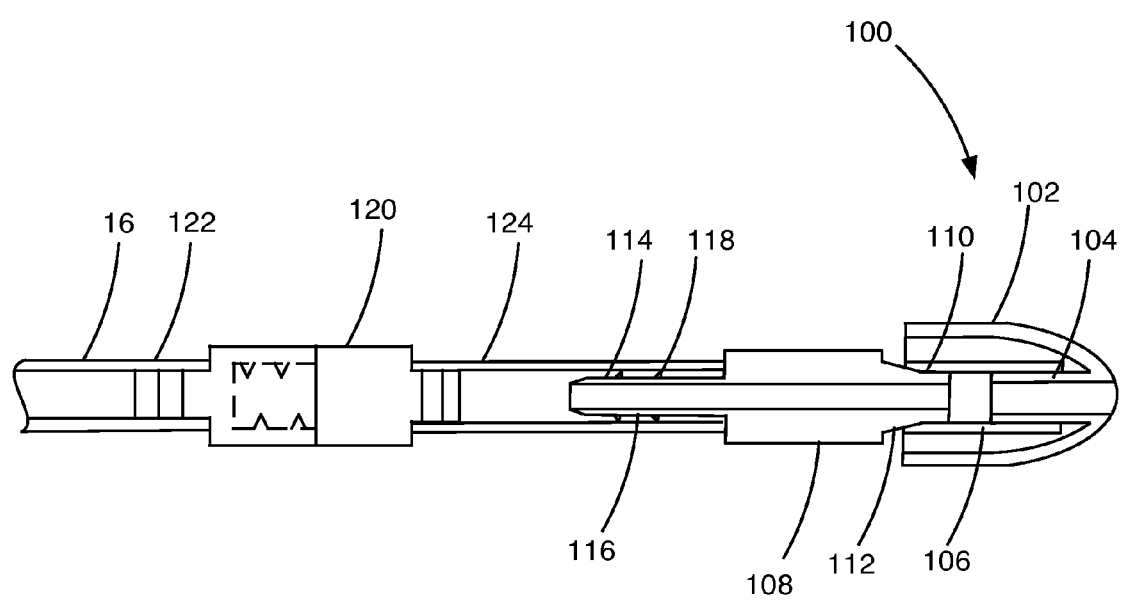
FIG. 7 shows a cross-sectional side view of a nozzle for use with a nasal rinsing apparatus in accordance with the principles of the present invention.

As shown in FIG. 7, another embodiment of a nozzle assembly 100 is illustrated in accordance with the principles of the present invention. The nozzle assembly 100 is comprised of a nozzle body 102 having an arcuate shape for fitting partially within a nostril of a user. An internal connecting tube 104 is integrally formed with the nozzle body 102. A flexible tube 106 is coupled by friction fit to the connecting tube 104. A hollow grip 108 is coupled at one end to the flexible tube 106 and configured for coupling to the tubing 16 (see FIG. 2). The grip 108 has a first distal end 110 with a partially tapered tubular section 112 for mating with the flexible tube 106 and being retained by a friction fit. The second proximal end 114 includes a tubular retaining portion 116 with a plurality of barbs 118 for holding the tubular relating portion 116 to the tube 16. A quick release connector 120 may also be intercoupled between separate sections 122 and 124 of the tube 16 so that the nozzle 102 and associated tubing 124 that may become contaminated during use can be sterilized or replaced without having to sterilize or replace the other components including the pump and container. The flexible tube 106 is provided to form a flexible connection between the nozzle body 102 and the grip 108. The grip 108 can thus be held by the user in a relatively rigid manner with the nozzle be articulatable relative to the nostril of the user for a more comfortable fit. In addition, use of the handle 108 provides a more comfortable and easer manner to hold the nozzle 102 against the nostril of the user.

Figure 8:
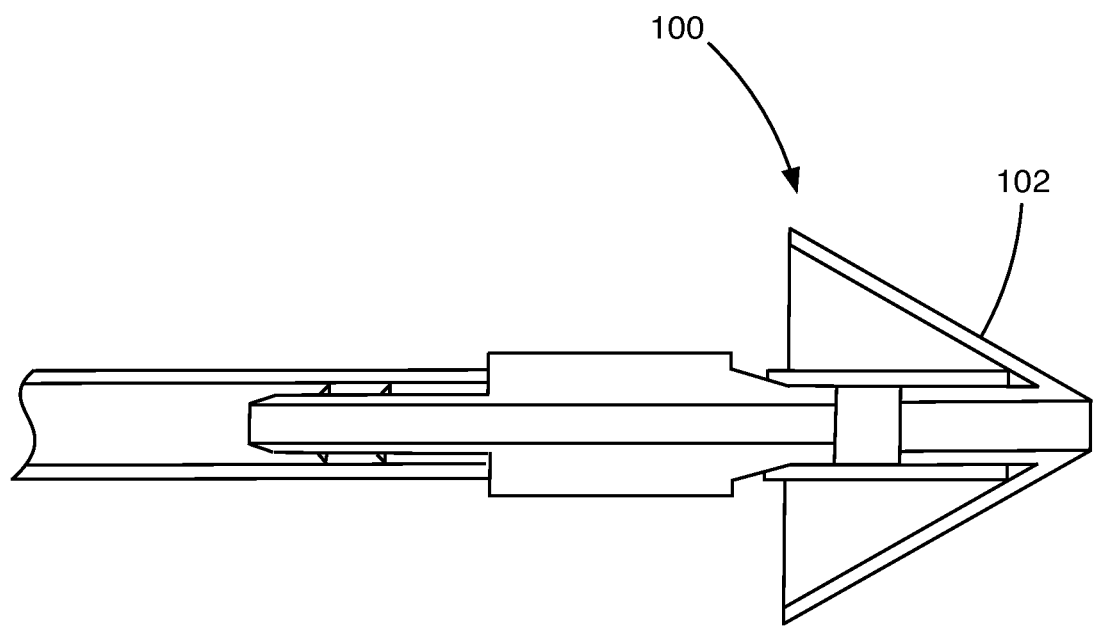
FIG. 8 shows a cross-sectional side view of another embodiment of a nozzle for use with a nasal rinsing apparatus in accordance with the principles of the present invention.

As shown in FIG. 8, another embodiment of a nozzle assembly 200 is illustrated. The nozzle assembly 200 is configured in a similar manner to the nozzle assembly 100 illustrated in FIG. 7 except that the nozzle body 202 has a conical shape. The conical shape provides a good seal between the nostril of the user and the nozzle body 202 during use. Thus, the shape of the nozzle body, while being describe herein as having particular shapes or configurations may be modified to any effective shape and is not limited to the shapes specifically described herein.

There is thus disclosed an improved apparatus for nasal rinsing and method of using the same. In the foregoing specification, the present invention has been described with reference to specific exemplary embodiments. Various modifications and changes may be made, however, without departing from the spirit and scope of the present invention as set forth in the claims, including combinations of elements of the various illustrated embodiments. The specification and figures are illustrative, not restrictive, and modifications are intended to be included within the scope of the present invention. Accordingly, the scope of the present invention should be determined by the claims and their legal equivalents rather than by merely the examples described.

For example, the steps recited in any method or process claims may be executed in any order and are not limited to the specific order presented in the claims. Additionally, the components and/or elements recited in any apparatus claims may be assembled or otherwise operationally configured in a variety of permutations and are accordingly not limited to the specific configuration recited in the claims.

Benefits, other advantages, and solutions to problems have been described above with regard to particular embodiments. Any benefit, advantage, solution to problem, or any element that may cause any particular benefit, advantage, or solution to occur or to become more pronounced are not to be construed as critical, required, or essential features or components of any or all the claims.

Use of the phrase "consisting essentially of" as may be used herein is intended to cover additional elements or functions that do not materially alter the specifically recited steps or elements. Thus, "consisting essentially of" is intended to encompass not only those components specifically listed, but also separate or additional components that do not materially alter the specifically recited functions or elements.

The terms "comprise", "comprises", "comprising", "having", "including", "includes" or any variations of such terms, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

What is claimed is:

1. An apparatus for dispensing a solution for nasal rinsing, comprising:
   a container having a bottom for resting on a surface and a top defining an opening, the container containing a saline solution for rinsing a nasal passage;
   a pump comprising a pump housing defining a hollow body and having an inlet at a distal end thereof disposed within the container and an outlet proximate the opening of the container, the pump housing coupled to the opening of the container, a pump handle coupled to a pump shaft slidably coupled to the pump housing, the pump shaft comprising a hollow tube in fluid communication with the pump housing and having a distal end coupled to a plunger disposed within the pump housing, the pump housing defining a hollow body for receiving the saline solution when the plunger is drawn from proximate a distal end of the pump housing to a proximate a proximal end of the pump housing and force the saline solution from the pump housing and through the pump shaft when the pump handle and thus the plunger is forced toward the distal end of the pump housing;
   an elongate flexible tube coupled at a first end to the pump handle, the elongate flexible tube receiving the saline solution from the container when the pump handle is depressed toward the pump housing; and a nozzle configured for mating with a nostril of a user, the nozzle coupled to a second end of the flexible tubing;

whereby pumping the handle in a first direction away from the container causes the saline solution to flow from the container, through the inlet of the pump housing and into the pump housing and pumping the handle in a second direction toward the container causes the saline solution to flow from the pump housing through the pump shaft, into the pump handle, through the elongate flexible tube and through the nozzle; and whereby the amount of saline solution and pressure under which the saline solution exits the nozzle can be controlled by selectively applying downward force of the handle toward the container.

2. The apparatus of claim 1, further comprising a first one-way valve disposed within the pump housing proximate a distal end thereof for preventing flow of the saline solution from the pump housing into the container when the pump handle is depressed, thereby causing the saline solution contained within the pump housing to be forced through the pump shaft and into the pump handle.

3. The apparatus of claim 2, wherein the first one-way valve comprises a first ball valve comprising a ball, a ball seat and a ball retaining structure, the ball residing between the ball seat and the ball retaining structure and movable between an open position and a closed position.

4. The apparatus of claim 2, further comprising a second one-way valve in fluid communication with the pump shaft for causing the saline solution to flow from the container into the pump housing when the pump shaft is extended from the pump housing.

5. The apparatus of claim 4, wherein the second one-way valve comprises a second ball valve comprising a ball, a ball seat and a ball retaining structure, the ball residing between the ball seat and the ball retaining structure and movable between an open position and a closed position.

6. The apparatus of claim 1, further comprising a biasing member disposed within the pump housing between a distal end of the pump housing and the plunger for forcing the plunger away from the distal end of the housing, to move the pump handle from a first position after the pump handle has been depressed to a second position away from the container when the pump handle is released.

7. The apparatus of claim 1, wherein a volume defined within the pump housing between the distal end of the housing and the plunger is at least one of about 20 cc, at least about 30 cc and at least about 50 cc.

8. The apparatus of claim 7, wherein the pump is configured to allow a single pump to continue from between about 0.1 and 2.0 seconds.

9. The apparatus of claim 1, wherein the elongate flexible tube has a length of approximately 24 inches.

10. The apparatus of claim 1, further comprising a nozzle grip coupled to the nozzle with a section of flexible tubing, the nozzle grip being positioned proximate the nozzle.

11. A method of dispensing a solution for nasal rinsing, comprising:

preparing a saline solution in a container having a bottom for resting on a surface and a top defining an opening, the container containing the saline solution for rinsing a nasal passage;

placing a nozzle configured for mating with a nostril of a user against a nostril, the nozzle coupled to an elongate flexible tube which is coupled to a pump comprising a pump housing defining a hollow body and having an inlet at a distal end thereof disposed within the container and an outlet proximate the opening of the container, the pump housing coupled to the opening of the container, a pump handle coupled to a pump shaft slidably coupled to the pump housing, the pump shaft comprising a hollow tube in fluid communication with the pump housing and having a distal end coupled to a plunger disposed within the pump housing, the pump housing defining a hollow body for receiving the saline solution when the plunger is drawn from proximate a distal end of the pump housing to a proximate a proximal end of the pump housing and force the saline solution from the pump housing and through the pump shaft when the pump handle and thus the plunger is forced toward the distal end of the pump housing; and pumping the pump handle of the pump that is coupled to the container to cause the saline solution to flow through the nozzle under controlled pressure into a nasal passage of a user;

whereby pumping the handle in a first direction away from the container causes the saline solution to flow from the container, through the inlet of the pump housing and into the pump housing and pumping the handle in a second direction toward the container causes the saline solution to flow from the pump housing through the pump shaft, into the pump handle, through the elongate flexible tube and through the nozzle; and whereby the amount of saline solution and pressure under which the saline solution exits the nozzle can be controlled by selectively applying downward force of the handle toward the container.

12. The method of claim 11, further comprising pumping the pump handle at a rate of between about 0.1 and 2 seconds per pump.

13. The method of claim 12, further comprising causing a flow of approximately 20 to 50 mL of saline solution to flow through the nozzle during each pump.

14. The method of claim 11, further comprising repeatedly pumping the pump handle at a rate of about 0.25 seconds per pump.

15. The method of claim 11, further comprising pumping between about 20 mL and about 50 mL of solution per pump.

16. The method of claim 15, further comprising repeatedly pumping the pump so that approximately 300 mL of solution is pumped into the nostril of the user.

17. The method of claim 16, further comprising placing the nozzle against the other nostril of the user and repeatedly pumping the pump so that approximately 300 mL of solution is pumped into the other nostril of the user.

18. The method of claim 11, further comprising grasping a nozzle grip coupled to the nozzle to hold the nozzle against the nostril of the user.

19. The method of claim 11, further comprising placing the container on a surface adjacent a sink, placing the nostril of the user over the sink and allowing the solution to flow from the nostril against which the nozzle is placed through the nasal passages of the user, out the opposite nostril of the user and into the sink.

20. The method of claim 11, further comprising forming the saline solution from water and dry ingredients in the form of iodized salt and sodium bicarbonate in a water to dry ingredient ratio of approximately 100:1.

* * * * *